United States Patent
Tiitta et al.

(10) Patent No.: US 7,814,799 B2
(45) Date of Patent: Oct. 19, 2010

(54) METHOD FOR THE DETERMINATION OF THE STRESSES OCCURRING IN WOOD WHEN DRYING

(75) Inventors: Markku Tiitta, Kuopio (FI); Reijo Lappalainen, Kuopio (FI); Pekka Miettinen, Kuopio (FI)

(73) Assignee: Korwensuun Konetehdas Oy, Kuopio (FI)

(*) Notice: Subject to any disclaimer, the term of this patent is extended or adjusted under 35 U.S.C. 154(b) by 416 days.

(21) Appl. No.: 12/074,457

(22) Filed: Mar. 3, 2008

(65) Prior Publication Data
US 2008/0148593 A1 Jun. 26, 2008

Related U.S. Application Data

(63) Continuation of application No. PCT/FI2006/000298, filed on Sep. 8, 2006.

(30) Foreign Application Priority Data

Sep. 9, 2005 (FI) .................................. 20050898

(51) Int. Cl.
*G01L 1/00* (2006.01)
(52) U.S. Cl. ...................................................... 73/781
(58) Field of Classification Search .................. 73/781, 73/597, 644
See application file for complete search history.

(56) References Cited

U.S. PATENT DOCUMENTS

| | | | |
|---|---|---|---|
| 4,107,599 A | * 8/1978 | Preikschat | 324/689 |
| 5,804,728 A | * 9/1998 | Beall et al. | 73/598 |
| 6,327,910 B1 | 12/2001 | Beall | 73/644 |
| 7,068,050 B2 | * 6/2006 | Steele et al. | 324/640 |
| 7,271,706 B2 | * 9/2007 | Lee | 340/384.2 |
| 7,383,730 B2 | * 6/2008 | Huang et al. | 73/597 |
| 2003/0146767 A1 | 8/2003 | Steele et al. | 324/640 |
| 2004/0124856 A1 | 7/2004 | Venter et al. | 324/664 |

FOREIGN PATENT DOCUMENTS

| | | |
|---|---|---|
| CA | 1080305 A1 | 6/1980 |
| EP | 0496885 A1 | 8/1992 |
| FI | 110640 B | 2/2003 |
| SU | 1041841 A1 | 9/1983 |

(Continued)

OTHER PUBLICATIONS

J.D. Booker et al., "Acoustic Emission Related to Strain Energy During Drying of Eucalyptus Regnans Boards", Journal Wood Science and Technology, vol. 29, No. 2, Feb. 1995, pp. 145-156.

(Continued)

*Primary Examiner*—Lisa M Caputo
*Assistant Examiner*—Octavia Davis
(74) *Attorney, Agent, or Firm*—Harrington & Smith

(57) ABSTRACT

The present invention relates to a method for the determination of the stresses occurring in wood when drying or being dried. With the method in accordance with the invention, electrodes are used to generate an electric field in drying wood in order to measure the electric complex spectrum using the impedance spectroscopy method while at the same time employing sensors to measure acoustic emissions from drying wood and using the results for calculating the parameters required for determining the stress state existing in the wood and for monitoring and/or controlling the drying process.

6 Claims, 2 Drawing Sheets

FOREIGN PATENT DOCUMENTS

WO  WO-91/07261  5/1991
WO  WO-96/28741  9/1996

OTHER PUBLICATIONS

Y. Kagawa et al., "Detection of Acoustic Emissions in the Process of Timber Drying", Accoustics Letters, vol. 3, No. 8, Apr. 1980, pp. 150-153.

R.M. Honeycutt et al., "Use of Acoustic Emissions to Control Drying Rate of Red Oak", Forest Products Research Society 1985, vol. 35, No. 1, Jan. 1985, pp. 48-50.

D.D. Bettinger et al., "Microprocessor Based System for the Detection and Characterization of Acoustic Emissions for Materials Testing", Industrial Electronics, Control, and Instrumentation, 1993, Proceedings of the IECON '93, International Conference on Nov. 15-19, 1993, vol. 3, pp. 2364-2367.

S.J. Kowalski et al., "The Identification of Fracture in Dried Wood Based on Theoretical Modelling and Acoustic Emission", Wood Sciencee Technology 38 (2004) pp. 35-52, Published online Mar. 16, 2004, Springer-Verlag 2004.

\* cited by examiner

METHOD FOR THE DETERMINATION OF THE STRESSES OCCURRING IN WOOD WHEN DRYING

CROSS REFERENCE TO RELATED APPLICATION

This application is a continuation of International Patent Application No. PCT/FI2006/000298 filed on Sep. 8, 2006.

The present invention relates to a method in accordance with claim 1 for the determination of the stresses occurring in wood when drying or being dried.

BACKGROUND OF THE INVENTION

Cracking that takes place in wood during drying is mainly due to the moisture gradient developing inside the wood that generates stresses within the wood because wood contracts non-uniformly when drying. The dried surface layer of wood shrinks more than the moister heartwood, resulting in cracks in the surface. Additionally, there is always a degree of microcracking involved when wood dries, which, if uncontrolled, will propagate and develop into macro cracks. The prevention of cracking or the limitation of the size of the cracks to the preferred level is of great importance financially.

Electrical methods have been widely used for the determination of wood moisture content because the effect of moisture on the electrical properties of wood is significant. At low moisture levels, for example, the electrical properties of wood change exponentially rather than linearly as a function of the moisture content. Two commonly used methods for measuring the moisture content of wood is the determination of the electrical resistance of wood and the measurement of the dielectricity of wood. When ohm-meters are used, the electrodes are inserted into the wood, meaning that the material must be partially broken. With measuring methods based on dielectricity, surface contact is usually enough, which makes this method non-destructive. In reality, the reliability of meters relying on surface contact is poor, which is largely due to the fact that the method is extremely sensitive to surface moisture.

The maximum limits for the measuring range of ohm-meters are determined by the saturation point of the wood fibres. At moisture contents exceeding the fibre saturation point, the cell cavities of wood contain free water in addition to the water bound to the grains, and thus the electrical resistance of wood does not, beyond this point, any longer really change as a function of the moisture content. With methods based on dielectricity, it is possible to measure wood moisture levels at moisture contents exceeding the fibre saturation point up to over 100%. In theory, the dielectric constant of wood increases until the cell cavities are completely filled with water. In reality, the accuracy of dielectric hygrometers decreases when the moisture content exceeds the fibre saturation point, which is, among other things, due to the fact that moisture distribution is usually great and a method relying on a single measurement frequency is highly sensitive to variations in the wood surface moisture content.

With commonly used surface hygrometers, the measurement is carried out at a single frequency, which makes the instruments sensitive to surface moisture. While this sensitivity changes as a function of frequency, it is considerable irrespective of the frequency used. If the, specimen being measured exhibits moisture distribution, it is not possible to give an accurate evaluation of the moisture content deeper in the specimen or of the average moisture content in the whole specimen based on the reading provided by the surface hygrometer.

Several scientific studies have shown that an acoustic emission method (hereinafter the AE method) can be used for monitoring the creation and propagation of cracks in various materials, including wood. Acoustic emissions are stress wave impulses generated on release of small amounts of energy, for example in connection with the growth of cracks and the deformation of material. Typically, acoustic signals of the ultrasonic frequency propagate in the material and are reflected and attenuated as well as generate various waveforms.

Normally, emission signals are detected with piezoelectric ultrasonic sensors that convert mechanical vibration into electric signals. The weak pulse received from the sensor is amplified with a pre-amplifier that transmits the amplified signal to the measuring system that typically consists of filters, amplifiers, and analyzers. Typical signal parameters to be analyzed are the number and amplitude of the signals. Also, the frequency content of signals has been used to advantage in the analyses.

The AE method has, in particular, been used in condition monitoring applications for machinery and equipment in the process industry, such as plastics and metals. In wood research, the AE method has been used for determining stresses present in living trees, determining the biological decomposition of wood, detecting termites, analyzing the propagation of cracks and crazes, monitoring wood drying, monitoring the drying of adhesives used in the manufacture of composite wood materials, determining the strength of wood in mechanical strength tests, determining the damage to wood caused by working, as well as for evaluating the condition of wood-working tools.

With the AE method, cracking can be measured quantitatively even before any visible macro cracks appear in the wood. The emissions generated by the cracks are proportional to the stresses appearing inside the wood.

The purpose of the present invention is to provide a method for the determination of the stresses occurring in wood when drying in order to overcome a number of drawbacks associated with the current methods. More specifically, the purpose of the invention is to provide a method that allows easy, efficient and reliable monitoring and/or control of wood drying by means of determining the stresses acting on the material.

SUMMARY OF THE INVENTION

With the method in accordance with the invention, electrodes are used to generate at least one electric field in drying wood, measure the electric complex spectrum using the impedance spectroscopy method while at the same time employing at least one sensor placed in the vicinity of the electrodes to measure acoustic emissions from drying wood and using the results for calculating the parameters required for determining the stress state existing in the wood. Additionally, the results obtained in this manner are used for monitoring and/or controlling drying. In the impedance spectroscopy method (hereinafter the IS method), a variable electric field is generated inside the specimen to be measured by means of electrodes. With the method in accordance with the present invention, the IS method is employed for the purpose of determining the stresses occurring in wood. The stress created in wood is determined on the basis of the electric dispersion of the wood material in a complex impedance spectrum that is affected by the properties of the wood, such as moisture content, moisture gradient, temperature, density, and structure. When the electric complex spectrum and acoustic properties are determined at the same time in accordance with the present invention, the stresses inside drying wood can be measured with greater accuracy than before and the results can be used to advantage in controlling drying in order to achieve wood products of superior quality.

In a preferred embodiment of the invention, the method is used simultaneously for monitoring wood drying with the IS method and micro cracking and macro-cracking during drying with the acoustic emission method.

By monitoring the responses from the AE and IS method simultaneously, it is possible to determine the stresses appearing in wood when drying with greater accuracy as well as to work out and optimize drying formulae for wood products of different size and type being dried or drying more efficiently in such a way that the final wood product is of high quality and free of all macro cracks.

For example, control can be implemented as follows. If the wood is drying too fast, the resulting high drying stresses occurring in the wood and the responses received with the IS and AE methods approach a critical value, after which micro cracks will propagate uncontrollably and may develop into macro cracks. If so, drying can be de-accelerated by reducing the temperature and/or increasing the air humidity, which will alleviate the stresses that will eventually lead to crack propagation. Conversely, drying can be accelerated by increasing the temperature or reducing the air humidity when the monitoring values fall clearly below said critical values. The critical limits will be selected according to the wood species and grade involved. By combining the two methods discussed here, it is possible to achieve greater accuracy in determination because, among other things, the acoustic signal propagating in wood as well as the electric impedance depend very much on the moisture content of wood. Moreover, the combined method allows simultaneous measurement of the changes in the mechanical and electrical properties of wood, which improves the accuracy of such determination. Unlike the conventional methods, the IS method is capable of measuring moisture content in the various layers of the wood, not only the moisture content of the gaseous atmosphere or that of individual isolated spots in the material.

In another preferred embodiment of the invention, the electric complex spectrum is measured with electrodes placed on the wood surface and/or in the immediate vicinity of the surface and/or moved relative to the wood surface and/or attached to the wood. This allows fully non-destructive measurement through the use of electrodes placed on the wood surface or its immediate vicinity or moved relative to it. Air-coupled measurement also permits contact-free determination ensuring that any substances migrating to the surface during drying, such a resin, do not soil the electrodes and affect the measurement as much as in full-contact measurement. With Air-coupled measurement, the electrodes do not interfere with the surface drying as much as surface electrodes. The electrodes can be attached to the wood in a number of ways. By using electrodes fixed to the wood, such as screws, it is possible to achieve a stable contact and have the electrodes placed at different depths in the wood.

In another preferred embodiment of the invention, the sensor measuring acoustic emissions is connected to the piece of wood being measured either directly or through air or with a wave conductor. Thus, a stable contact, high sensitivity and great spatial accuracy are achieved in full-contact measurement. At the same time, wave conductors allow the collection of acoustic emissions from several drying pieces of wood over a large area. As in impedance spectroscopy measurement, air-coupled acoustic emission measurement offers the advantage of eliminating any errors due to the substances released from wood during drying and keeping the electrodes free from contamination.

In another preferred embodiment of the invention, the drying of the wood is controlled by adjusting the drying conditions, such as temperature and humidity, air-flow and fogging, or by using any other known method or by making use of the control capabilities available for special drying. Wood drying is controlled with due regard to, and by making use of, the results obtained by means of said methods. Wood drying is controlled online while giving due consideration for ongoing changes.

In accordance with the invention, the AE sensor is placed near the electrode, making it possible to combine the results of the measurements. Additionally, the preferred embodiment makes use of several measuring points in which the sensor/ electrode is placed. By using several measuring points, it is possible to provide a spatial determination of the stresses appearing in the various parts of the drying wood.

DESCRIPTION OF DRAWINGS

In the following, the invention is presented in greater detail with reference to the attached drawings where

FIG. 1 shows a piece of wood 2 placed in the drying chamber 8. Electrodes 1 required by the IS method have been attached to the wood or placed in its immediate vicinity, including the acoustic emission sensor 3. Additionally, the schematic shows the measuring device 5 to which the electrodes are connected, as well the amplifier 6 to which the sensor 3 is wired. Furthermore, the system includes the control unit 4, to which the measuring device and amplifier have been connected. The control unit incorporates the necessary technology for modifying the received signals, processing the data, determining the stress state of the drying wood and adjusting the drying conditions. The control unit is connected to the drying chamber control device 7 that controls the drying chamber adjustments in a conventional manner, for example in the way described hereinafter. In this method, use is made of one or several IS electrode pairs and one or several acoustic emission sensors. The number of IS electrodes and acoustic emission sensors may vary from one embodiment to another as preferred and they can be placed in the desired and appropriate manner relative to the drying piece of wood. Full-contact or contact-free measurement can be used with both methods.

The schematic in FIG. 2 shows, in principle, the same equipment as in FIG. 2. Additionally, FIG. 2 illustrates a wireless data transmission device 9 and the stand-alone computer 10. In this example, the electronic measurement and control units 4, 5 and 6, are placed close to the process circuit in the temperature and humidity controlled box 11.

The following section provides a description of the invention by means of examples.

EXAMPLE 1

Monitoring and Control Method for Normal Drying

Figure 2:
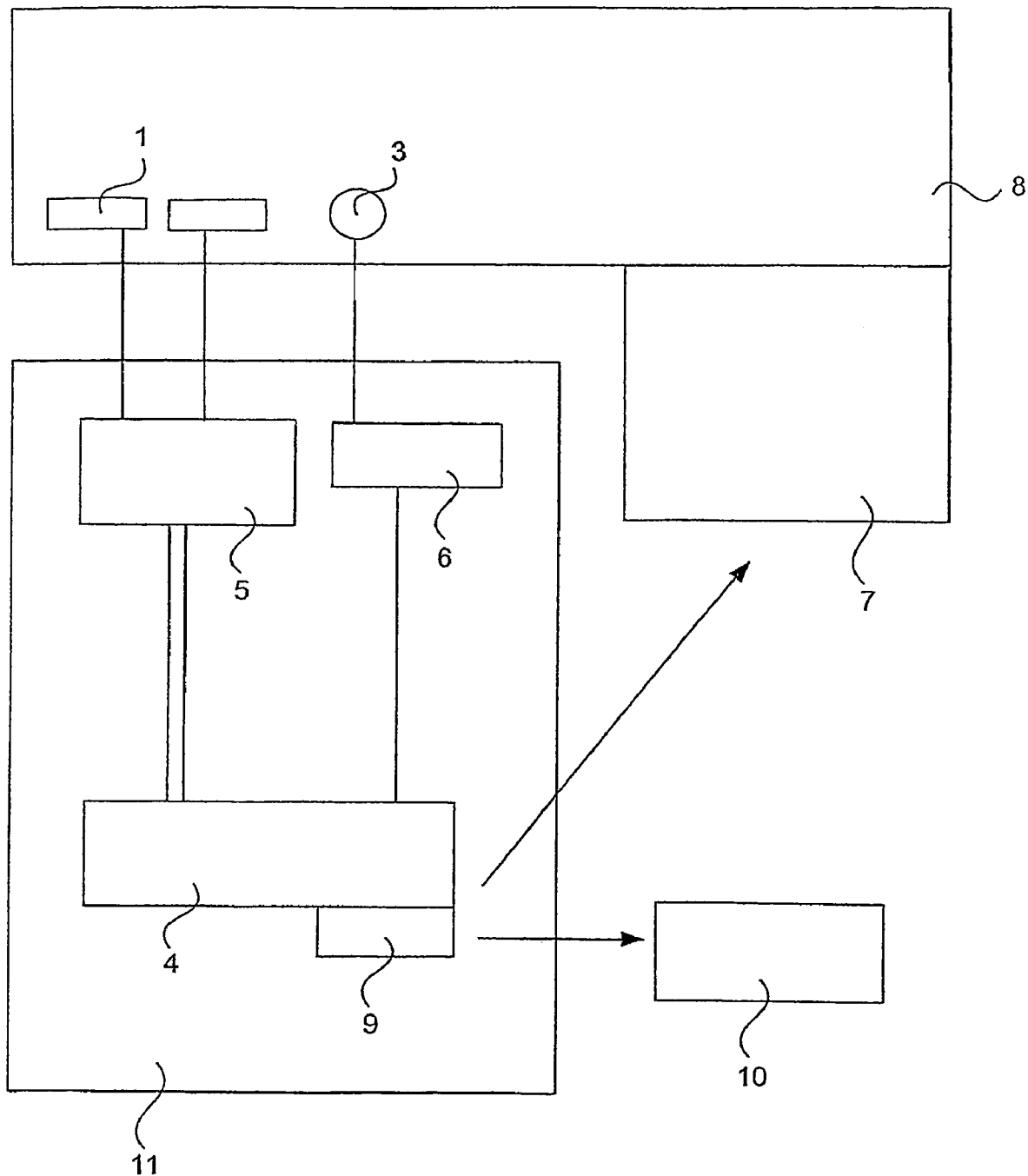
FIG. 2 is a schematic of another embodiment of the method in accordance with the invention.

The following section provides a description of the first embodiment of the invention with reference to FIG. 2 in which a piece of drying wood placed inside the drying kiln 8 is monitored with the IS electrodes 1 and acoustic emission sensor 3. In this example, the electrodes consist of metallic 10 mm screw electrodes attached to the side of the sawn timber at a preferable spacing of 50 mm. The electrodes are made of stainless steel. Before the measurements are started, the impedance measurement is calibrated using open and shot circuit corrections. The ultrasonic sensor with a diameter of about 10 mm to be used in the measurements in accordance with the AE method is attached to the wood by wedging it next to the electrode. Consequently, the stresses appearing in the wood during drying can be determined from the same position as the moisture content. The electrodes are connected to the impedance spectrometer 5 with which the IS measurement can be carried out. The electric complex impedance is determined from the reference values constituting the spectrometer output values and the measurement readings from the control unit 4 for each measuring frequency. The sensor to be used in the AE method is connected to the pre-amplifier 6 whose output consists of the amplified acoustic signal that is fed to the control unit 4.

In this case, the control unit 4 consists of a portable computer fitted with an analogue/digital converter that converts the measured signals suitable for use in the control software. The computer includes a software application that monitors the measurement channels for the IS and AE methods on a continual basis and transmits the measurement data to the monitoring computer 10 using the wireless Bluetooth connection 9. The same computer is used for controlling the wood drying system 7 that includes air humidity and temperature control systems. In this case, data is transmitted to the monitoring computer and the drying control unit via a wireless connection. The wireless connection makes it possible to have the drying process monitored indoors at the preferred location. A fixed-line connection can also be used in other embodiments.

For each species of wood, there are specific limit values that may not be exceeded. These limit values are based on theoretical calculations that are also verified experimentally.

Measurement is activated before drying is started in order to obtain initial parameters for the drying wood. The IS method can be used for assessing the wood moisture content while at the same time the AE method is used to determine the stresses acting inside the wood before drying. Once drying starts, the changes taking place in the impedance spectrum are monitored at least at two frequencies in terms of the electric impedance and phase. In this case the determination takes place at the frequencies 5 kHz, 20 kHz, 200 kHz, and 800 kHz. Additionally, the prevalence, amplitude and frequency content of acoustic emissions are measured on a continuous basis.

The stresses appearing in drying wood can, for instance, be determined at said frequencies by measuring the absolute value and phase angle of the electric impedance and the number, energy and frequency content of acoustic emissions. By measuring said values, it is possible to monitor the progress of drying and the stresses produced in the process. In the present example, the determination of the critical limit value is based on measured values, the variation in the values and the rate of change in the values during drying. In order to optimize the drying result, the values so determined may be used one by one, meaning that when any of the values approaches the limit value specified for such a parameter, the drying process can be de-accelerated. With the IS measurement method, the effective measuring range at individual frequencies is different depending, among other things, on the moisture gradient and moisture content. This makes it possible to evaluate the stresses appearing in the surface and deeper layers of the wood and to achieve the optimum measurement result in the interest of premium quality. For each specified measurement parameter, there is a specific range of calibrated values within which they may vary without exceeding the critical limit value. When the wood moisture gradient is known from the IS method, the AE signals can be used to determine whether they are transmitted by way of the acoustic energy or frequency content from the surface or inner layers of the wood because signals travelling in the wood at an ultrasonic frequency are strongly attenuated and filtered in such a way that the highest frequencies are filtered more effectively than others.

EXAMPLE 2

Application of Multiple Variable Methods

In this example of an embodiment of the invention, the method is similar to example 1 or examples 3 through 16, with reference made to FIG. 2, except that the method used for analyzing the measurements is the multiple variable method. The multiple variable method may, for example, involve the use of multiple variable regression, principal component regression (PCR) or partial least squares (PLS). By making measurements on the calibration samples, it is possible to formulate a multiple variable matrix that shows, in separate columns, the actual stress field measured from each calibration sample as well as the values for the specified IS and AE parameters. The stress state generated in the process can be determined by means of a standard destructive test method at the various stages of drying. By using one of said multiple variable methods, the error between the stress function application and the actual stress can be minimized. This yields a multiple variable matrix that contains the factors for the parameters as well as the constant factors. The stresses occurring in wood during drying are determined by measuring the IS and AE parameters from the sample and using the stress functions based on the specified matrix factors.

EXAMPLE 3

Monitoring Method

In this example of an embodiment of the invention, the method is similar to examples 1 and 2 or examples 4 through 16, with reference made to FIG. 2, except that in this application the link to the drying control system is lacking. Thus, the method, as presented in this example, only serves the purpose of monitoring the drying process and outputting measurement and stress readings to the monitoring device. This application may be used, for instance, when the drying rate is to be optimized, the drying process is to be monitored or the optimum drying of wood species other than those already calibrated is to be studied.

EXAMPLE 4

Control Method

In this example of an embodiment of the invention, the method is similar to examples 1 through 3 or examples 5 through 16, with reference made to FIG. 2, except that no monitoring system is provided in this application. As a result, the method only serves the purpose of controlling drying. However, this embodiment of the invention can be used for routine drying or when the drying rate is not critical and the quality of the wood is to be optimized, instead.

EXAMPLE 5

Compression Drying

Figure 1:
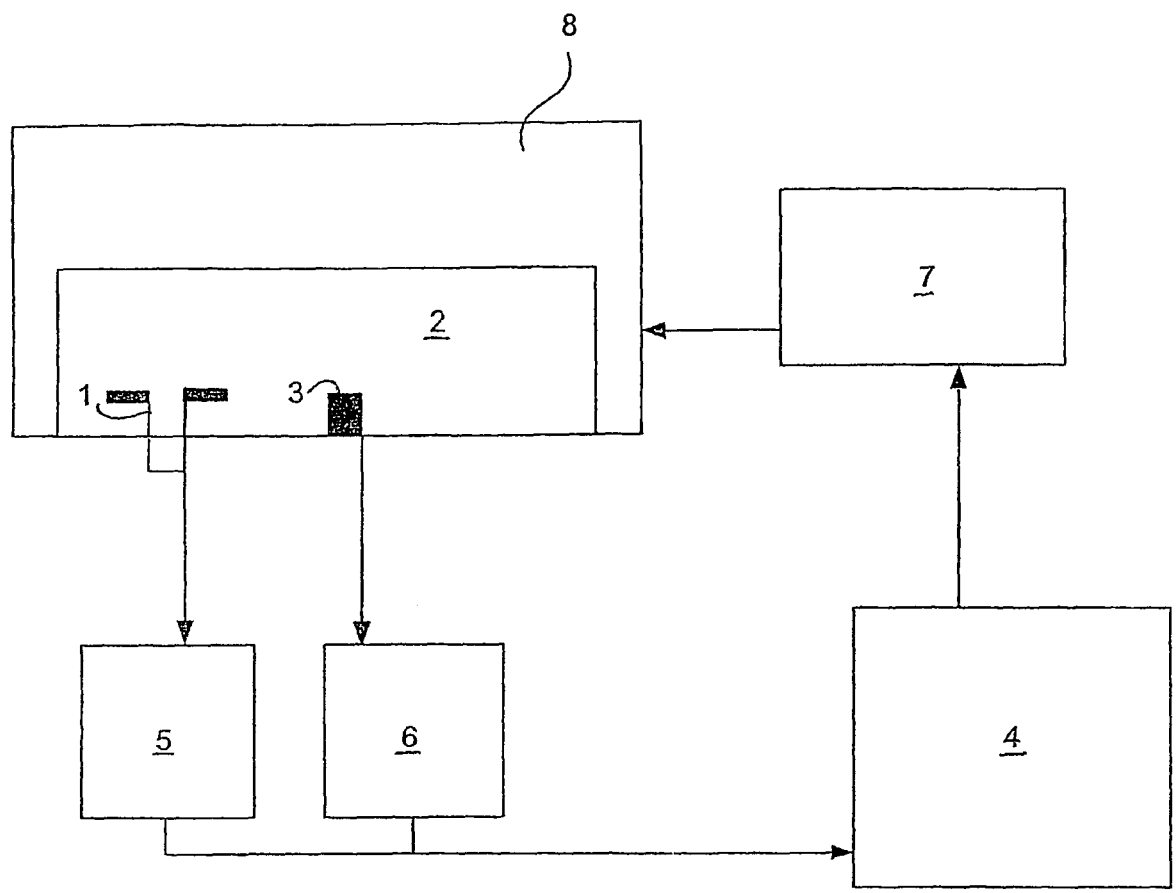
FIG. 1 is a schematic of one embodiment of the method in accordance with the invention.

In this example of an embodiment of the invention, the method is similar to examples 1 through 4 or examples 7 through 16, and reference is made to FIG. 1. In this embodiment, the method is configured to determine the stresses appearing in wood during compression drying, which is affected not only by the drying process but also by the compressive force applied. The method can be used for determining the acoustic emissions caused by the compressive force in order to optimize the compressive force and degree such that the stress to which the piece of wood is subjected remains low enough throughout the process and no critical macro cracks can develop as a result of the compressive force or its intensity or the drying process.

EXAMPLE 6

Heat Modification

In this example of an embodiment of the invention, the method is similar to examples 1 through 5 or examples 7 through 16, and reference is made to FIG. 1. In this embodiment, the method is configured to determine the stresses occurring in wood during heat treatment, which is affected, among other things, by the intensity of the treatment. The method can be used for determining acoustic emissions generated in the course of heat treatment that can be used to advantage to control the heat treatment process in such a way that the stress to which the piece of wood is subjected remains low enough throughout the process and no critical macro cracks can develop. More specifically, this embodiment can be used for determining the stresses caused by heat and structural changes. Unlike in the preceding examples, here the stresses appearing in the wood are determined by using the IS and AE methods side by side.

EXAMPLE 7

Methods for Collecting Acoustic Emission Data

In this example of an embodiment of the invention, the method is similar to examples 1 through 6 or examples 7 through 16, and reference is made to FIG. 1. Here the AE sensor 3 is connected to the drying process with a wave guide. The wave guide may consist of any material that carries acoustic signals effectively with low attenuation. In compressive drying, the wave conductor may consist of metal press plates used in the process. In standard drying or heat treatment, various types of wave guides may be used that can be attached to the drying wood as desired. If necessary, the wave guides may be attached to several pieces of drying wood, allowing the acoustic emissions to be measured from several pieces at the same time. Unlike in the embodiments discussed above, the perforated metal plates used in the compressive drying process can be used for collecting the acoustic emission data.

EXAMPLE 8

Air-Coupled AE Method

In this example of an embodiment of the invention, the method is similar to examples 1 through 7 or examples 9 through 16, and reference is made to FIG. 1. Here the AE sensor 3 is air-coupled to the drying process with sensors whose acoustic impedance is adjusted as close to that of air as possible in order to minimize the interference at the sensor-to-air interface. In this fashion, emission signals of extremely low energy can be measured through the air while at the same time the measurement of acoustic emissions is made possible.

EXAMPLE 9

IS Surface Electrode Application

In this example of an embodiment of the invention, the method is similar to examples 1 through 8 or examples 12 through 15, and reference is made to FIG. 1. In this embodiment, surface electrode compatible with the IS method are attached to the wood surface. By using capacitative surface electrodes, it is possible to considerably reduce the electrode polarization caused by fresh wood. The electrodes can be shaped to the required size depending on the type of the drying wood; electrodes adapting to the form of the surface can also be used. Typically, rectangular or circular electrodes placed side by side are used. In the IS method, the effective measurement depth depends, above all, on the distance between the electrodes. Unlike in the prior art, the stresses occurring in the wood are measured using the IS and AE methods simultaneously.

EXAMPLE 10

Contact-Free IS Method

In this example of an embodiment of the invention, the method is similar to examples 1 through 8 or examples 12 through 16, and reference is made to FIG. 1. In this embodiment, electrodes are positioned as close as possible to the drying piece of wood without actually touching it. A typical distance from the wood surface is 0.1 to 2 mm to ensure that the moisture gradient can be determined. For example, the determination of the moisture gradient can be implemented by making the measurement using either contact-free surface electrodes or electrodes capable of measuring through the wood.

EXAMPLE 11

IS Pin Electrode Application

In this example of an embodiment of the invention, the method is similar to examples 1 through 8 or examples 12 through 15, and reference is made to FIG. 1. In this embodiment, pin or screw electrodes attached to the wood at different depths are used in order to allow the measurement of the stress state caused by the wood moisture gradient at the same time with the AE measurement. In this example, the impedance can only be determined at one frequency but a more accurate result can be obtained by using several frequencies, thus effectively eliminating the measurement error caused by the electrode polarization of the pins and/or screws.

EXAMPLE 12

IS Method Model Application

In this example of an embodiment of the invention, the method is similar to examples 1 through 11 or examples 13 through 16, and reference is made to FIG. 1. In this embodiment, a broad impedance spectrum is measured extending at least from the frequency band of 10 kHz to 1 MHz. An electrical model, the parameters of which are used for determining the stress, is fitted in the complex spectrum graph. For example, the Gauss-Newton or Nelder-Mead optimization method may be used in the model application.

EXAMPLE 13

Optional Control Systems for Drying

In this example of an embodiment of the invention, the method is similar to examples 1 through 12 or examples 14 through 16, and reference is made to FIG. 1. In this embodiment, adjustment of the airflow used for drying or some other method of controlling the process parameters, such as temperature or air humidity, is used to control the drying process. If, for example, water vapour spraying is used in the drying process, it can be adjusted. If drying is carried out using ultrasonic, electrical or microwave technology, the drying power of these devices can be controlled as well.

EXAMPLE 14

Multiple Sensor Application

In this example of an embodiment of the invention, the method is similar to examples 1 through 13 or examples 15 through 16, and reference is made to FIG. 1. In this embodiment, several acoustic emission sensors and IS electrodes are used for the purpose, among other things, of demonstrating the stresses appearing inside the pieces of wood being dried in different locations in the kiln or illustrating the stress distributions in different directions.

EXAMPLE 15

Various Wood Product Applications

In this example of an embodiment of the invention, the method is similar to examples 1 through 14 or example 16, and reference is made to FIG. 1. In this embodiment, one or several scanning IS method electrodes are used that is/are moved relative to the wood surface. This makes it possible to determine the stresses appearing in the pieces of wood being dried at different locations in the kiln or illustrating the stress distributions in different directions.

The practical applications of the invention are not limited to the above examples, instead, the invention and its embodiments may be varied within the scope of protection provided by the claims.

The invention claimed is:

1. A method for determination of stresses occurring in wood when drying or being dried, in which
    electrodes are used to create at least one changing electric field in drying wood,
    measuring an electric complex spectrum using a impedance spectroscopy method,
    while at the same time employing at least one sensor placed in the vicinity of the electrodes to measure acoustic emissions from drying wood, and
    using the results for calculating the parameters required for determining the stress state prevailing in the wood, with the results obtained in this manner being used for monitoring and/or controlling drying.

2. A method in accordance with claim 1, which
    is used to monitor the drying of wood by simultaneously measuring the electric complex spectrum using the impedance spectroscopy method while at the same time monitoring a micro-cracking and macro-cracking appearing in wood during drying.

3. A method in accordance with claim 1, in which
    the electric complex spectrum is measured with electrodes placed on a wood surface and/or in the immediate vicinity of the surface and/or moved relative to the wood surface and/or attached to the wood.

4. A method in accordance with claim 1, in which
    the sensor measuring acoustic emissions is connected to the piece of wood being measured either directly or through air or by wave conductor.

5. A method in accordance with claim 1, in which
    electric complex spectrum and acoustic emissions are measured from several measuring points.

6. A method in accordance with claim 1, in which
    the drying of the wood is controlled by adjusting the drying conditions, such as temperature and humidity, air flow and fogging, or by using any other known method or by making use of the control capabilities available in special drying.

* * * * *